(12) United States Patent
Brabec et al.

(10) Patent No.: US 7,225,035 B2
(45) Date of Patent: May 29, 2007

(54) MULTIPOLAR MEDICAL ELECTRICAL LEAD

(75) Inventors: Scott J. Brabec, Elk River, MN (US); Douglas S. Hine, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 357 days.

(21) Appl. No.: 10/876,003

(22) Filed: Jun. 24, 2004

(65) Prior Publication Data

US 2005/0288761 A1 Dec. 29, 2005

(51) Int. Cl.
*A61N 1/05* (2006.01)

(52) U.S. Cl. .................... 607/122; 607/119; 607/116

(58) Field of Classification Search ............ None
See application file for complete search history.

(56) References Cited

U.S. PATENT DOCUMENTS

| | | | |
|---|---|---|---|
| 4,848,352 A | 7/1989 | Pohndorf et al. .......... 128/642 |
| 5,800,465 A | 9/1998 | Thompson et al. ............ 607/9 |
| 5,935,160 A | 8/1999 | Auricchio et al. .......... 607/122 |
| 5,999,858 A | 12/1999 | Sommer et al. ............ 607/122 |
| 6,192,280 B1 | 2/2001 | Sommer et al. ............ 607/122 |
| 6,278,894 B1 | 8/2001 | Salo et al. ................ 600/547 |
| 6,295,475 B1 | 9/2001 | Morgan ................... 607/122 |
| 6,363,288 B1 | 3/2002 | Bush et al. ............... 607/122 |
| 6,430,447 B1 | 8/2002 | Chitre et al. |
| 6,847,845 B2 * | 1/2005 | Belden .................... 607/37 |
| 6,901,289 B2 * | 5/2005 | Dahl et al. ................. 607/9 |
| 6,920,361 B2 * | 7/2005 | Williams ................. 607/122 |
| 7,031,777 B2 * | 4/2006 | Hine et al. ............... 607/122 |
| 2002/0065544 A1 | 5/2002 | Smits et al. |
| 2002/0123784 A1 | 9/2002 | Westendorp ............. 607/122 |
| 2003/0109914 A1 | 6/2003 | Westlund et al. ......... 607/122 |
| 2003/0139794 A1 | 7/2003 | Christopher et al. |
| 2003/0220676 A1 | 11/2003 | Helland |
| 2004/0064173 A1 | 4/2004 | Hine et al. ............... 607/122 |

FOREIGN PATENT DOCUMENTS

| | | |
|---|---|---|
| EP | 0 571 797 B1 | 9/1998 |
| WO | WO 02/053225 A2 | 7/2002 |
| WO | WO 057311 A2 | 7/2003 |

* cited by examiner

*Primary Examiner*—Carl Layno
(74) *Attorney, Agent, or Firm*—Michael C. Soldner; Carol F. Barry; Girma Wolde-Michael

(57) ABSTRACT

A pacing lead includes a first pacing cathode coupled to a first conductor, a second pacing cathode coupled to a second conductor, and a flexible anode coupled to a third conductor. The flexible anode has a length less than approximately 10 millimeters and is spaced apart from and proximal to the first pacing cathode and spaced apart from and distal to the second pacing cathode. The spacing between the anode and the first pacing cathode is approximately equal to the spacing between the anode and the second pacing cathode.

25 Claims, 4 Drawing Sheets

MULTIPOLAR MEDICAL ELECTRICAL LEAD

TECHNICAL FIELD

The present invention is directed to implantable medical devices and more particularly to medical electrical leads including a plurality of electrodes.

BACKGROUND

Implantable medical electrical stimulation and/or sensing leads are well known in the field of cardiac stimulation and monitoring, for example cardiac pacing and/or cardioversion/defibrillation, and in other fields of electrical stimulation or monitoring, for example of the central nervous system. In the field of cardiac stimulation and monitoring, lead electrodes are positioned at an endocardial or epicardial site and an implantable pulse generator (IPG), pacemaker or cardioverter/defibrillator, or a monitor is coupled to the heart through one or more of such endocardial or epicardial leads. Means for implanting such cardiac leads are known to those skilled in the art of pacing and defibrillation therapy.

More recently, medical electrical leads have been constructed to include a plurality of pacing and/or sensing electrodes from which one or more of the electrodes may be selected in order to optimize electrical stimulation therapy and/or monitoring. Additionally leads adapted for deep brain stimulation, and other leads adapted to stimulate other muscles of the body may include a plurality of electrodes from which one or more electrodes may be selected to optimize therapy.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
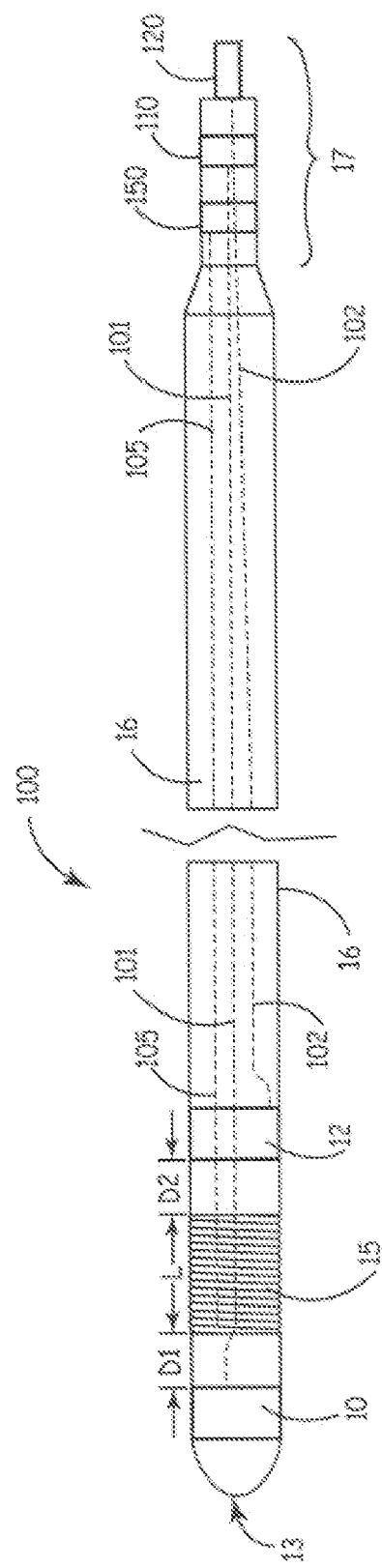
FIG. 1 is a plan view of a medical electrical lead according to one embodiment of the present invention.

FIG. 1 is a plan view of a medical electrical lead 100 according to one embodiment of the present invention. FIG. 1 illustrates lead 100 including a elongate body 16 carrying a first elongate conductor 101, a second elongate conductor 102 and a third elongate conductor 105, each illustrated schematically with dashed lines; according to one embodiment, lead body 16 is formed of a multilumen insulative sheath, either silicone or polyurethane, and conductors 101, 102, 105 from cabled bundles of MP35N wires. FIG. 1 further illustrates lead body 16 terminated at a proximal end by a connector 17, which includes electrical contacts 120, 110 and 150 coupled to conductors 102, 101 and 105, respectively; lead 100 further includes electrodes 12, 10 and 15 formed about a distal portion of lead body 16, proximal to a distal end 13 of lead 100, and coupled to contacts 120, 110 and 150, respectively, via conductors 102, 101 and 105. Connector 17, an in-line lead connector, is just one embodiment of many connector types that may be incorporated; the scope of the present invention includes any type of lead connector known to those skilled in the art for coupling a pulse generator device, such as a pacemaker, to a medical electrical lead.

According to some embodiments of the present invention the distal portion of lead body 16 is sized to fit within a coronary vein in order to pace and sense from an epicardial surface of a heart; thus an outer diameter of electrodes 10, 12 and 15 is less than approximately 2 mm and according to a particular embodiment a diameter of flexible electrode 15 is approximately 1.3 mm. Furthermore, although not shown in FIG. 1, the distal portion of lead body 16 may include one or more preformed bends to urge electrodes 10 and 12 into contact with the epicardial surface; an example of such a lead distal portion is described by Sommer et al. in U.S. Pat. No. 5,999,858, which is incorporated by reference herein in its entirety.

Figure 2:
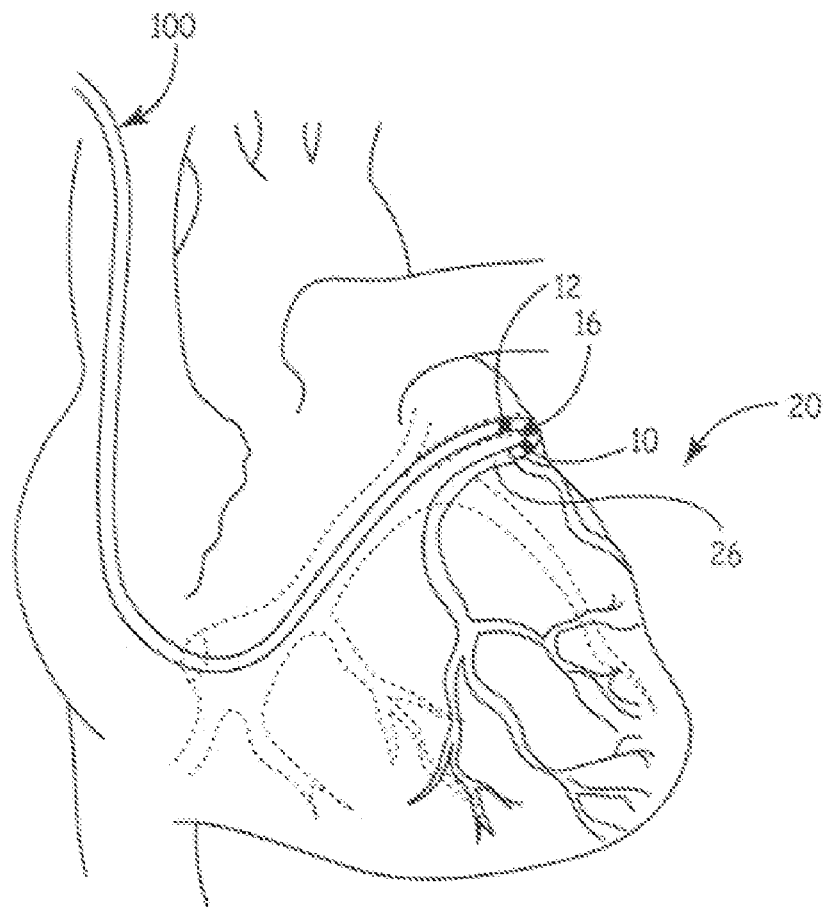
FIG. 2 is a schematic showing the lead of FIG. 1 implanted within a coronary vasculature.

An implanted position of lead electrodes is often constrained by coronary vasculature anatomy, thus embodiments of the present invention provide at least two options for a pacing electrode position. FIG. 2 is a schematic showing the lead 100 implanted within a coronary vasculature. FIG. 2 illustrates electrodes 10, 12 and 15 positioned in a great cardiac vein 28 wherein either a pair formed by electrode 10 and electrode 15, electrode 10 as cathode and electrode 15 as anode, or a pair formed by electrode 12 and electrode 15, electrode 12 as cathode and electrode 15 as anode, may be selected for stimulation/pacing of a left ventricle 20. According to some embodiments of the present invention, the selection is based either upon a pacing/stimulation threshold, lower being more desirable, or upon an absence of phrenic nerve stimulation resulting from the pacing from the pair, or upon hemodynamic response of the heart, for example as observed via echocardiography, or upon a combination of any of these factors; selection at time of implant would be determined by delivering test pulses to each of the pairs and observing the results. According to another aspect of the present invention, one of electrodes 10 and 12, which is not selected, may be used to sense an evoked response to pacing/stimulation delivered by the pair including the selected one of electrodes 10 and 12; the sensing may be bipolar, for example the unselected electrode in conjunction with electrode 15 or another electrode included on another implanted lead, or unipolar.

According to common knowledge of those skilled in the art, a bipolar pacing pair including an anode having a greater geometric surface area than that of the cathode results in lower pacing thresholds. According to embodiments of the present inventions a ratio of a surface area of electrode 15 to a surface area of either electrode 10 or electrode 12 is greater than approximately 3:1 or greater than or equal to approximately 6:1. In order to accommodate an enlarged surface area for electrode 15, embodiments of the present invention include anode electrode 15 having a flexibility to navigate within the coronary vasculature; electrode 15 may be formed by a coiled conductive wire, as illustrated, or by a layer of a conductive polymer. Examples of suitable wire materials include, but are not limited to, platinum and tantalum, and examples of conductive polymers include, but are not limited to metallic or carbon filled silicone, polyacetylene, polypyrrole and polyanaline. Embodiments of the present invention may further include those wherein electrode 15 includes a coating to reduce post-pace polarization; examples of such coatings include, but are not limited to, titanium nitride, platinum black and iridium oxide.

Returning now to FIG. 1, a distance D1 between electrode 10 and flexible electrode 15 is approximately equal to a distance D2 between electrode 12 and flexible electrode 15 according to embodiments of the present invention; distances D1 and D2 may be between approximately 5 mm and approximately 15 mm or between approximately 9 mm and approximately 15 mm. Furthermore, according to embodiments of the invention, a length L of electrode 15 is less than approximately 10 mm, preferably between approximately 3 mm and approximately 10 mm. According to an exemplary embodiment, electrode 15 has a length L of approximately 8 mm and a diameter of approximately 1.3 mm while electrodes 10 and 12 each have a length of approximately 1 mm and a diameter of approximately 1.6 mm.

Figure 3:
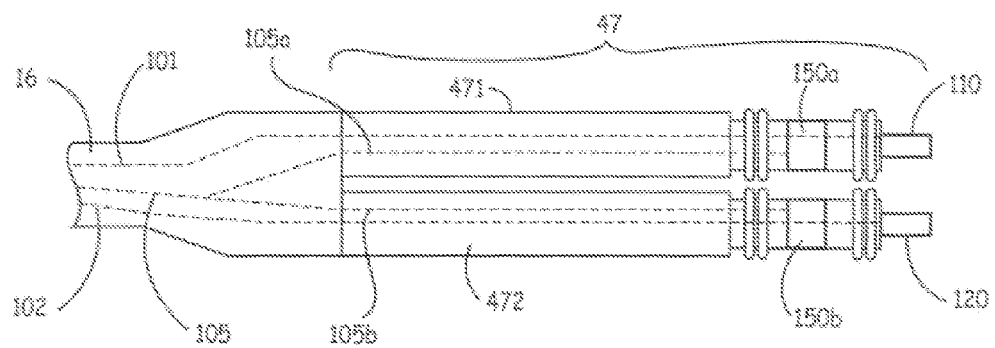
FIG. 3 is a plan view of a lead connector according to another embodiment of the present invention.

FIG. 3 is a plan view of a lead connector 47 according to another embodiment of the present invention. FIG. 3 illustrates bifurcated lead connector 47 terminating a proximal end of lead body 16 and including a first leg 471 and a second leg 472; according to one embodiment of the present invention first leg 471 and second leg 472 each conform to the IS-1 industry standard. FIG. 3 further illustrates conductor 101 and a branch 105*a* of conductor 105 extending into first leg 471 to couple with contact 110 and a contact 150*a*, respectively, and conductor 102 and a branch 105*b* of conductor 105 extending into second leg 472 to couple with contact 120 and a contact 150*b*, respectively. According to the illustrated embodiment, once lead 100 is implanted and one of electrodes 10 and 12 (FIGS. 1 and 2) has been selected as the cathode to function in conjunction with anode electrode 15, the connector leg corresponding with the selected cathode, for example leg 471 for cathode 10 or leg 472 for cathode 12, is connected to a pulse generator device. The non-selected leg may be capped according to means known to those skilled in the art.

Figure 4:
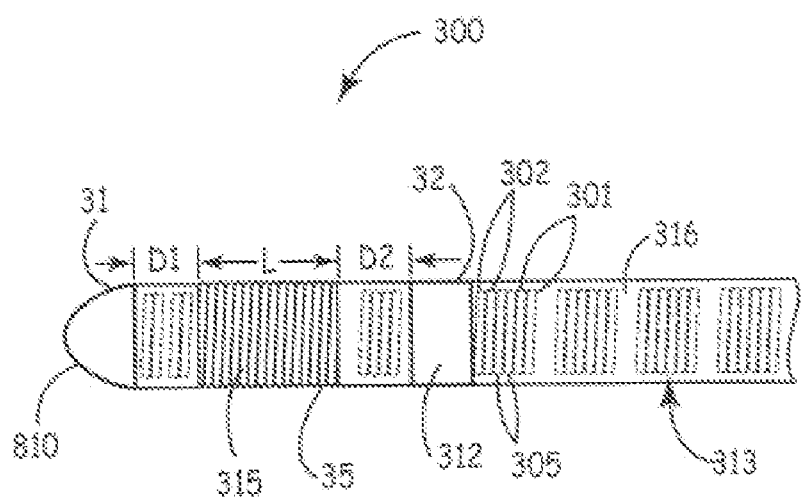
FIG. 4 is a plan view of a distal portion of a medical electrical lead according to another embodiment of the present invention.

FIG. 4 is a plan view of a distal portion of a medical electrical lead 300 according to another embodiment of the present invention. FIG. 4 illustrates a lead body 316 in the form of an elongate insulative sheath carrying a multi-filar coiled conductor 313 shown by dashed lines; coiled conductor 313 includes three sets of filar pairs 301, 302 and 305 electrically isolated from one another. According to the illustrated embodiment first filar pair 301 is coupled to tip electrode 310 at a junction 31, second filar pair 302 is coupled to a proximal electrode 312 at a junction 32, and third filar pair 305 is coupled to a flexible anode electrode 315 at junction 35. Junctions 31, 32 and 35 may be formed according to methods known to those skilled in the art, for example by crimps, stakes or welds. According to an exemplary embodiment of the present invention, filar pairs 301, 302 and 305 are isolated from one another by means of a hydrolytically stable polyimide coating formed about each filar of two or all of the pairs; a similar multi-filar conductor construction is described in co-pending patent application U.S. 2003/0216800, which is incorporated by reference in its entirety herein. According to yet another embodiment each conductor may be formed as an independent coil according to a coaxial construction well known to those skilled in the art. Although not shown, tip electrode 310 may include a longitudinally extending lumen, in communication with a lumen of coiled conductor 313, for passage of guidewire therethrough, and a tip seal; such a configuration is described by Sommer and Hine in U.S. Pat. No. 6,192,280 which is incorporated by reference herein in its entirety.

In the foregoing detailed description, the invention has been described with reference to specific embodiments. However, it may be appreciated that various modifications and changes can be made without departing from the scope of the invention as set forth in the appended claims.

What is claimed is:

1. A medical electrical lead, comprising:
   an elongate lead body including a first conductor, a second conductor and a third conductor extending therein and electrically isolated from one another;
   a first cathode electrode coupled to the first conductor;
   a second cathode electrode coupled to the second conductor; and
   a flexible anode electrode having a length less than approximately 10 millimeters and a surface area greater than a surface area of each of the first cathode electrode and the second cathode electrode, being coupled to the third conductor, spaced apart from and proximal to the first cathode electrode and spaced apart from and distal to the second cathode electrode, the spacing between the anode electrode and the first cathode electrode being approximately equal to the spacing between the anode electrode and the second cathode electrode.

2. The lead of claim 1, wherein a length of the flexible anode electrode is between approximately 3 millimeters and approximately 10 millimeters.

3. The lead of claim 2, wherein the length is approximately 8 millimeters.

4. The lead of claim 1, wherein an outer diameter of the flexible anode electrode is between approximately 0.75 millimeters and approximately 2 millimeters.

5. The lead of claim 4, wherein the outer diameter is approximately 1.3 millimeters.

6. The lead of claim 1, wherein a length of the flexible anode electrode is between approximately 3 millimeters and approximately 10 millimeters and an outer diameter of the flexible anode electrode is between approximately 0.75 millimeters and approximately 2 millimeters.

7. The lead of claim 1, wherein the first cathode electrode is positioned proximal to a distal end of the lead body.

8. The lead of claim 1, wherein the first cathode electrode terminates a distal end of the lead body.

9. The lead of claim 1, wherein the flexible anode electrode comprises a conductive polymer.

10. The lead of claim 1, wherein the flexible anode electrode comprises a coiled conductive wire.

11. The lead of claim 1, wherein the flexible anode electrode includes a coating to reduce post-pace polarization.

12. The lead of claim 1, wherein a ratio of a surface area of the flexible anode electrode to a surface area of each of the first cathode electrode and the second cathode electrode is greater than approximately 3:1.

13. The lead of claim 12, wherein the ratio is greater than or equal to approximately 6:1.

14. The lead of claim 1, wherein the spacing between the flexible anode electrode and the first cathode electrode is between approximately 5 millimeters and approximately 15 millimeters.

15. The lead of claim 1, wherein the spacing between the flexible anode electrode and the first cathode electrode is between approximately 9 millimeters and approximately 15 millimeters.

16. The lead of claim 1, further comprising an in-line connector terminating a proximal end of the lead body; the in-line connector comprising a first contact coupled to the first conductor, a second contact coupled to the second conductor and a third contact coupled to the a third conductor; wherein the third contact is positioned distal to the first contact and the second contact.

17. The lead of claim 1, further comprising a bifurcated connector terminating a proximal end of the lead body; the bifurcated connector including a first contact coupled to the first conductor and a second contact coupled to the third conductor, the first contact and the second contact positioned on a first leg, and a third contact coupled to the second conductor and a fourth contact coupled to the third conductor, the third contact and the fourth contact positioned on a second leg.

18. The pacing lead of claim 17, wherein the first contact terminates a proximal end of the first leg and the third contact terminates a proximal end of the second leg.

19. The pacing lead of claim 17, wherein each leg of the bifurcated connector conforms to an industry standard.

20. A method for delivering a pacing pulse to a heart, the method comprising the steps of:
    positioning a distal portion of a pacing lead within a coronary vein, the distal portion including a first pacing cathode, a second pacing cathode and a flexible anode having a length less than approximately 10 millimeters and a surface area greater than a surface area of each of the first pacing cathode and the second pacing cathode, the flexible anode spaced apart from and proximal to the first pacing cathode and spaced apart from and distal to the second pacing cathode, the spacing between the anode and the first pacing cathode being approximately equal to the spacing between the anode and the second pacing cathode;
    selecting a one of the first pacing cathode and the second pacing cathode to form a bipolar pair with the flexible anode;
    delivering a pacing pulse to the heart via the bipolar pair.

21. The method of claim 20, further comprising the steps of: applying a test pacing pulse to each of the first pacing cathode and the second pacing cathode; and
    measuring pacing thresholds of the first pacing cathode and the second pacing cathode; and
    wherein the step of selecting the one from the first pacing cathode and the second pacing cathode is based upon the pacing thresholds.

22. The method of claim 20, further comprising the steps of:
    applying test pacing pulses to each of the first pacing cathode and the second pacing cathode; and
    observing for phrenic nerve stimulation resulting from the pacing pulses; and
    wherein the step of selecting the one from the first pacing cathode and the second pacing cathode is based upon an absence of phrenic nerve stimulation.

23. The method of claim 20, further comprising the steps of: applying test pacing pulses to each of the first pacing cathode and the second pacing cathode; and
    observing a hemodynamic response of the heart resulting from the pacing pulses; and
    wherein the step of selecting the one from the first pacing cathode and the second pacing cathode is based upon the hemodynamic response.

24. The method of claim 20, further comprising the step of sensing an evoked response of the pacing pulse from the bipolar pair by means of another of the first pacing cathode and the second pacing cathode that is not selected.

25. The method of claim 20, wherein:
    the step of selecting the one from the first pacing cathode and the second pacing cathode comprises selecting a connector leg from a first connector leg and a second connector leg of a bifurcated connector terminating a proximal end of the lead;
    wherein the first connector leg includes a first contact coupled to the first conductor and a second contact coupled to the third conductor and the second connector leg includes a third contact coupled to the second conductor and a fourth contact coupled to the third conductor.

* * * * *